United States Patent
Bahl et al.

(10) Patent No.: US 9,775,819 B2
(45) Date of Patent: Oct. 3, 2017

(54) ORAL SOLID DOSAGE FORM CONTAINING NANOPARTICLES AND PROCESS OF FORMULATING THE SAME USING FISH GELATIN

(75) Inventors: Deepak Bahl, Monmouth Junction, NJ (US); Kieran James Crowley, Highland Park, NJ (US); Danny Yu, Somerville, NJ (US)

(73) Assignee: R.P. SCHERER TECHNOLOGIES, LLC, Las Vegas, NV (US)

( * ) Notice: Subject to any disclaimer, the term of this patent is extended or adjusted under 35 U.S.C. 154(b) by 351 days.

(21) Appl. No.: 12/560,813

(22) Filed: Sep. 16, 2009

(65) Prior Publication Data

US 2011/0064812 A1 Mar. 17, 2011

(51) Int. Cl.
| | |
|---|---|
| A61K 31/192 | (2006.01) |
| A61K 9/20 | (2006.01) |
| A61K 9/19 | (2006.01) |
| A61K 9/51 | (2006.01) |

(52) U.S. Cl.
CPC .............. *A61K 31/192* (2013.01); *A61K 9/19* (2013.01); *A61K 9/2077* (2013.01); *A61K 9/5169* (2013.01)

(58) Field of Classification Search
USPC ........................................................ 424/400
See application file for complete search history.

(56) References Cited

U.S. PATENT DOCUMENTS

| | | | |
|---|---|---|---|
| 5,145,684 A | 9/1992 | Liversidge et al. | |
| 5,302,401 A | 4/1994 | Liversidge et al. | |
| 5,510,118 A | 4/1996 | Bosch et al. | |
| 5,817,334 A | 10/1998 | Schmidt et al. | |
| 5,932,245 A | 8/1999 | Wunderlich et al. | |
| 5,968,251 A | 10/1999 | Auweter et al. | |
| 6,066,337 A | 5/2000 | Allen et al. | |
| 6,316,029 B1 | 11/2001 | Jain et al. | |
| 6,509,040 B1 | 1/2003 | Murray et al. | |
| 6,548,170 B2 | 4/2003 | Perrier et al. | |
| 6,709,669 B1 | 3/2004 | Murray et al. | |
| 7,687,071 B1 * | 3/2010 | Heger et al. | 424/489 |
| 2002/0110599 A1 | 8/2002 | Auweter et al. | |
| 2004/0076666 A1 | 4/2004 | Green et al. | |
| 2004/0156895 A1 | 8/2004 | Pruitt et al. | |
| 2005/0031691 A1 | 2/2005 | McGurk et al. | |
| 2006/0035871 A1 * | 2/2006 | Auweter et al. | 514/169 |
| 2008/0207775 A1 | 8/2008 | Musaeus et al. | |
| 2008/0220071 A1 | 9/2008 | Jensen et al. | |
| 2008/0299205 A1 | 12/2008 | Mayer et al. | |
| 2009/0098207 A1 | 4/2009 | Malakhov et al. | |
| 2009/0163447 A1 | 6/2009 | Maggio | |
| 2010/0055246 A1 | 3/2010 | Ahn | |
| 2013/0336915 A1 | 12/2013 | Mayer et al. | |
| 2013/0337078 A1 | 12/2013 | Mayer et al. | |

FOREIGN PATENT DOCUMENTS

| | | |
|---|---|---|
| CA | 2353809 | 6/2000 |
| DE | 19637517 A1 | 3/1998 |
| JP | H04500803 A | 2/1992 |
| JP | 2006-508136 A | 3/2006 |
| JP | 2008-506780 A | 3/2008 |
| WO | 90/03795 A1 | 4/1990 |
| WO | 99/38496 A1 | 8/1999 |
| WO | 00/61141 A2 | 10/2000 |
| WO | WO 00/61117 * | 10/2000 |
| WO | 2004/043440 A1 | 5/2004 |
| WO | 2006/014626 A2 | 2/2006 |
| WO | 2006/119107 A2 | 11/2006 |
| WO | 2008/030209 A2 | 3/2008 |
| WO | 2008/137831 A1 | 11/2008 |
| WO | 2009/013466 A1 | 1/2009 |

OTHER PUBLICATIONS

Surh et al. "Properties and stability of oil-in-water emulsions stabilized by fish gelatin", Food Hydrocolloids, p. 596-606 (2006).*
Klus Zwiorek, "Gelatin Nanoparticles as delivery system", (2006).*
Liu, R., "Water-Insoluble Drug Formulation", CRC Press, 2nd ed., p. 1 (2008).
Abdelwahed, W., et al., "Freeze-drying of Nanoparticles: Formulation, Process and Storage Considerations", Advanced Drug Delivery Reviews, vol. 58, Issue 15, pp. 1688-1713 (2006).
Elan: Technology Focus brochure available at http:www.elan.com/EDT/ (date unknown, after Jul. 2005).
Kesisoglou, F., et al., "Nanosizing-Oral Formulation Development and Biopharmaceutical Evaluation", Advanced Drug Delivery Reviews, vol. 59, Issue 7, pp. 631-644 (2007).
Full Prescribing Information, Rapamune (Wyeth) (date unknown).
Scientific Discussion, Rapamune (Oct. 21, 2004) (date unknown).
Full Prescribing Information, EMEND (Merck) (date unknown).
Scientific Discussion, EMEND (2004).
Product Information Literature for TRICOR (Abbott) (date unknown).
Product Information Literature for Triglide (First Horizon) (date unknown).
International preliminary report on patentability issued in corresponding PCT application No. PCT/US2010/048588—5 pages, (Mar. 20, 2012).
Dai et al., "Nanosizing of a drug/carrageenan complex to increase solubility and dissolution rate," International Journal of Pharmaceutics, vol. 342, No. 1-2, pp. 201-207 (2007).
Karim et al., "Fish gelatin: properties, challenges, and prospects as an alternative to mammalian gelatins," Food Hydrocolloids, vol. 23, No. 3, pp. 563-576 (2009).

* cited by examiner

*Primary Examiner* — Ernst V Arnold
*Assistant Examiner* — Kyung Sook Chang
(74) *Attorney, Agent, or Firm* — Fitzpatrick, Cella, Harper & Scinto

(57) ABSTRACT

An oral solid dosage form containing nanoparticles is made by (a) reducing the particle size of at least one pharmaceutically active ingredient dispersed in a solution containing fish gelatin to form a nanosuspension and (b) freeze-drying the nanosuspension of step (a) to form the oral solid dosage form.

19 Claims, No Drawings

ORAL SOLID DOSAGE FORM CONTAINING NANOPARTICLES AND PROCESS OF FORMULATING THE SAME USING FISH GELATIN

BACKGROUND OF THE INVENTION

Field of the Invention

This invention relates to an oral solid dosage form containing nanoparticles. This invention also relates to a process of formulating the oral solid dosage form using fish gelatin.

Description of Related Art

Oral drug delivery typically requires drug products to release drug molecules to form a solution in the gastrointestinal tract, so that drug can be absorbed across the gut wall and enter the systemic circulation. For reasons of product efficacy and safety, drug molecule release should take place in a controlled manner, with a release profile that meets the therapeutic requirements of the product. Most oral products aim for fast and complete release of drug in the gastrointestinal tract in order to generate a fast onset of action along with the most efficient delivery of drug molecule to the biological target.

Experts in the fields of drug discovery and drug development have noted that new drug molecules under development in recent years increasingly possess poor water solubility. Estimates of more than 40% of new drug molecules exhibiting poor water solubility have been documented. See Water Insoluble Drug Formulation, Rong Liu ed., CRC Press, 2nd ed., p. 1 (2008). The prevalence of poorly water soluble drug molecules creates a significant challenge for development of viable oral drug products. The reason for this problem is that poor water solubility can limit the speed and extent to which drug molecules can enter solution or dissolve in the gastrointestinal tract. The technical challenge of formulating poorly water soluble drugs can actually limit some drugs from reaching the market, thus denying patients new products.

A proven approach to improving the dissolution properties of poorly water soluble drug molecules is to reduce particle size of the solid drug, as increased surface area of the dissolving drug particles correlates with increased dissolution rates. Reduction of particle size to the submicron or nanoparticle range produces dramatic increases in surface area and thus the greatest opportunity for dissolution rate enhancement via this mechanism. Therefore, nanoparticle drug delivery can provide faster dissolution, improved bioavailability and ultimately enhanced clinical efficacy.

The advantages of using nanoparticles for oral drug delivery, especially for dosing poorly soluble drug molecules, are well known and have been documented for over 20 years. Despite this, the present inventors believe there are only about four commercial pharmaceutical oral solid dosage formulations in the United States that allege to contain nanoparticles, which suggests that there are technical challenges associated with developing stable nanoparticulate products. Known commercial oral solid dosage formulations are Rapamune® (Wyeth Pharmaceuticals Inc., Philadelphia, Pa.), Emend® (Merck & Co., Whitehouse Station, N.J.), TriCor® (Abbott Laboratories, North Chicago, Ill.), and Triglide™ (Sciele Pharma Inc., Atlanta, Ga.).

The primary problem with developing solid nanoparticle drug delivery systems is the tendency of nanoparticles to re-aggregate either rapidly during processing or on extended storage, which results in increased particle size and thus reduced efficacy. The aggregation problem is typically overcome using stabilizing excipients categorized as steric stabilizers (e.g., synthetic polymers) and/or electrostatic stabilizers (e.g., surfactants). The known commercial products noted above all use wet milling technology to create nanosuspensions, followed by spray drying of the nanosuspension onto a solid substrate phase of a size and dimension suitable for processing into a single-unit dosage form (e.g., tablet or capsule). Spray drying is a general term that may include recognized processes such as spray coating or spray granulation, whereby a nanosuspension is sprayed onto a solid substrate under conditions that cause rapid volatilization and removal of the liquid component to leave dried solid phase coated on the solid substrate.

Freeze-drying is an alternate process to spray drying that can convert a nanosuspension into the solid state, although this technology is not known to have been used in conventional nanoparticulate products. The aggregation problem is greater for a system that undergoes freeze-drying due to the intense physical forces experienced during the freezing and lyophilization steps of the freeze-drying process. Conventional solutions to address the aggregation problem typically involve complex manufacturing procedures, requiring isolation of a dried nanoparticle intermediate material and/or adjustment of the excipient composition after milling but before unit dosage form processing.

U.S. Pat. No. 5,932,245 describes the preparation of colloidal nanosols using a precipitation method with gelatin or its derivatives acting as nanoparticle stabilizer. The process involves stabilizing a colloidally dispersed solution of the active substance by partly or fully setting the iso-ionic point (equivalent to a neutral charge) between the gelatin and the surface charged active substance particles. There is, however, no disclosure or suggestion of using fish gelatin as a nanoparticle stabilizer during nanomilling and/or as a nanoparticle stabilizer during freeze-drying.

U.S. Pat. Nos. 5,145,684 and 5,510,118 describe wet milling processes to generate nanoparticles of low solubility drugs that use non-crosslinked surface modifiers to maintain particle size in the submicron range. Preferred surface modifiers include nonionic and anionic surfactants, but both disclosures indicate that surface modifiers may be selected from an extended list of pharmaceutical excipients that includes gelatin. There is, however, no disclosure or suggestion of using fish gelatin as a nanoparticle stabilizer during nanomilling and/or as a nanoparticle stabilizer during freeze-drying.

U.S. Patent Application Publication No. 2005/0031691 discloses compositions containing an active agent of less than about 2000 nm, at least one surface stabilizer, and a gel-forming agent, wherein gelatin functions as a water-retention aid to facilitate gelling in the dosage form. This system is claimed to provide compositions that can be molded into a variety of dosage forms. There is, however, no disclosure or suggestion of using fish gelatin as a nanoparticle stabilizer during nanomilling and/or as a nanoparticle stabilizer during freeze-drying.

The use of freeze-drying to convert a liquid nanosuspension into solid product with favorable dispersion properties (interchangeably described as fast-dispersing, fast-dissolving, fast disintegrating, rapidly disintegrating) is disclosed in WO99/38496, U.S. Pat. No. 5,302,401, WO 2004/043440, and U.S. Pat. No. 6,316,029. All disclosures indicate that gelatin may be included in the dosage form. However, there is no disclosure or suggestion regarding the specific benefits associated with one source of gelatin, such as gelatin extracted from fish.

WO99/38496 discloses gelatin among a long list of potential fast-dissolve matrix forming agents; however, there is no disclosure or suggestion of using fish gelatin during nano-suspension formation or as the nanoparticle stabilizer during manufacture of the fast-dissolve matrix.

U.S. Pat. No. 5,302,401 discloses the use of gelatin as a nanoparticle surface modifier stabilizer. However, a cryo-protectant (defined in U.S. Pat. No. 5,302,401 as an agent that protects from nanoparticle agglomeration caused by lyophilization) is disclosed as a separate component, which is preferably a carbohydrate. In addition, the cryoprotectant molecule is added to the pre-formed nanosuspension, suggesting that formula modifications between nanomilling and freeze-drying are critical to the successful formation of freeze-dried nanoparticles.

WO 2004/043440 also discloses the use of one or more surface stabilizer molecules, such as gelatin, in combination with pullulan (a polymeric carbohydrate) to form fast-disintegrating tablets containing nanoparticles using a lyophilization process. Pullulan is added to the pre-prepared nanosuspension before freeze-drying, with no description of adding pullulan prior to nanosuspension formation either as a surface stabilizer or for any other function. There is, however, no disclosure or suggestion of using fish gelatin as a nanoparticle stabilizer during nanomilling and/or as a nanoparticle stabilizer during freeze-drying.

U.S. Pat. No. 6,316,029 discloses the use of at least one surface stabilizer (with gelatin identified as an example) in combination with a water-soluble or water dispersible excipient (with gelatin identified as an example) processed to form a rapidly disintegrating dosage form containing nanoparticles. However, it does not disclose or suggest using fish gelatin as a nanoparticle stabilizer during nanomilling and/or as a nanoparticle stabilizer during freeze-drying. In addition, it does not disclose the need for a stabilizing agent to ensure nanoparticle size is retained during freeze-drying.

U.S. Pat. No. 6,709,669 discloses the preparation of fast-dispersing dosage forms using freeze-drying that contain pharmaceutical active ingredient and fish gelatin as a carrier. The advantages of using fish gelatin in this manner are identified as faster disintegration times, better taste and mouthfeel, and shorter manufacturing process times. However, it does not disclose or suggest a solid dosage form containing nanoparticles or the advantages of using fish gelatin in particle size reduction to form nanoparticles or freeze-drying of nanoparticle systems. In addition, there is no disclosure or suggestion of fish gelatin's stabilization properties of any kind, including nanoparticle stabilization.

The present inventors are unaware of any prior art that teaches or suggests the formation of a nanoparticulate solid oral dosage form using fish gelatin as both a nanoparticle stabilizer during nanomilling as well as a nanoparticle stabilizer during freeze-drying. Also, there is no known disclosure or suggestion of a process to manufacture nanoparticulate solid oral dosage forms without the need for significant adjustment of the qualitative and quantitative excipient composition between the nanomilling and freeze-drying steps. For example, information in the public domain regarding the manufacturing process of Rapamune® describes that the pharmaceutically active ingredient sirolimus is reduced by wet milling to nanometer dimensions in the presence of a stabilizer. Then, the nanodispersion is added to a sugar coating suspension and coated onto inert tablet cores previously overcoated with shellac. Another example is the manufacturing process for Emend®, for which a slurry of water, the pharmaceutically active ingredient aprepitant, and hydroxypropylcellulose (steric stabilizer) and sodium lauryl sulfate (ionic stabilizer) are media-milled to form a colloidal dispersion. To convert to a solid dosage form, sucrose is added to the dispersion followed by spraying the dispersion onto microcrystalline cellulose beads. Both processes clearly involve substantial changes in the qualitative (i.e., number of excipients) and quantitative (i.e., ratio of excipients) between the step of forming a nanodispersion and the step of forming a solid dosage form containing nanoparticles. See, product-specific scientific discussion documents available from the European Medicines Agency website at http://www.emea.europa.eu/. As can be seen, current commercial compositions and processes for nanoparticulate products are complex. Further, those skilled in the art will recognize that these compositions or processes are not appropriate for all pharmaceutically active ingredients.

Currently, a need exists for an alternate oral solid dosage form containing nanoparticles that is produced by a process that does not involve complex manufacturing procedures.

SUMMARY OF THE INVENTION

The present invention is directed to a method of preparing an oral solid dosage form containing nanoparticles, the process comprising the steps of: (a) reducing the particle size of at least one pharmaceutically active ingredient dispersed in a solution containing fish gelatin to form a nanosuspension; and (b) freeze-drying the nanosuspension of step (a) to form the oral solid dosage form.

The present invention is also directed to an oral solid dosage form containing nanoparticles made by a process comprising the steps of: (a) reducing the particle size of at least one pharmaceutically active ingredient dispersed in a solution containing fish gelatin to form a nanosuspension; and (b) freeze-drying the nanosuspension of step (a) to form the oral solid dosage form.

The present invention is also directed to a freeze-dried oral solid dosage form comprising at least one nanoparticulate active ingredient and fish gelatin.

DETAILED DESCRIPTION OF THE INVENTION

The present invention relates to an oral solid dosage form containing fish gelatin and a pharmaceutically active ingredient in nanoparticulate form. The present invention further relates to an efficient, robust method of making such a form without the need for excipient composition adjustment during the process steps. In other words, the same excipient—fish gelatin—can be used to facilitate particle size reduction and freeze-drying steps.

The first embodiment of the present invention is directed to a method of preparing an oral solid dosage form containing nanoparticles, the process comprising the steps of: (a) reducing the particle size of at least one pharmaceutically active ingredient dispersed in a solution containing fish gelatin to form a nanosuspension; and (b) freeze-drying the nanosuspension of step (a) to form the oral solid dosage form.

As used herein, "nanoparticles" or "nanoparticulate" refers to particles possessing a particle size distribution mainly in the sub-micron region, as demonstrated by an average and/or median particle size value less than about 1 micron; more preferably, "nanoparticles" or "nanoparticulate" refers to particles having the d50 preferred (discussed below) for purposes of the present invention. As used herein, "solid dosage form" refers to a unit-dose pharmaceutical product that exhibits primarily solid-state physical properties (i.e., dense, non-flowing, non-gaseous) when stored, handled and administered to patients. As used herein, "oral" refers to administration to or by way of the mouth.

In the first step of the inventive method, at least one pharmaceutically active ingredient is dispersed in a solution containing fish gelatin and processed to form a nanosuspension. The process used to reduce particle size may be any high-energy size reduction process including, but not limited to, wet milling or homogenization. A wet milling process typically uses a media mill such as a Dyno® Mill (Glen Mills Inc., Clifton, N.J.) that circulates the suspension through a chamber containing beads made from extremely hard, durable and essentially inert materials (e.g., zirconium). The high-energy movement and collisions of milling media with suspended pharmaceutically active ingredient lead to significant reductions in particle size of the pharmaceutically active ingredient. A homogenization process uses the combined energy from high pressure, high shear and high stress to reduce particle size of suspended phase, as can be achieved using a laboratory high-pressure homogenizer such as from Niro Soavi (Bedford, N.H.) or the M-110Y Microfluidizer® manufactured by Microfluidics International Corp. (Newton, Mass.). As used herein, "nanosuspension" refers to nanoparticles dispersed and uniformly suspended in a solution.

The solution in which the pharmaceutically active ingredient is dispersed (and ultimately, after size reduction, in which the nanoparticles are suspended) can be formed by any known means. Most typically, the fish gelatin is added to a suitable solvent. Suitable solvents include, without limitation, water, alcohols (e.g., methanol, ethanol, isopropanol, t-butyl alcohol), glycerine, polyethylene glycol, lipid oils (e.g., olive oil, peanut oil, or any lipid mixture with mono-, di- and/or tri-glycerides as the primary component), and combinations thereof. Water is the preferred solvent as the pharmaceutically active ingredients most amenable to formulation as nanoparticles are typically poorly water soluble.

Other pharmaceutical excipients may also be added to the solvent containing fish gelatin. An example is the inclusion of an ingredient or ingredients that modify or buffer pH to maintain optimal conditions for pharmaceutically active ingredient suspension. Other pharmaceutical excipients may also be included in the solution prior to pharmaceutically active ingredient addition for purposes of affecting a product attribute other than the formation and stabilization of nanoparticles during the process described herein. Examples of such pharmaceutical excipients include, but are not limited to, bulking agents (e.g., lactose monohydrate, anhydrous lactose, sucrose, trehalose, fructose, glucose, maltose, mannitol, isomalt, glycine, maltodextrin, microcrystalline cellulose), chemical stability enhancers (e.g., anti-oxidants, chelating agents, ion-exchange resins, α-, β-, or γ-cyclodextrins or substituted ring α-, β-, or γ-cyclodextrins) disintegrants (e.g., croscarmellose sodium, crospovidone, sodium starch glycolate, starch, modified starch), viscosity modifiers (e.g., bovine gelatin, porcine gelatin, alginates, carrageenan gum, gellan gum, guar gum, xanthan gum, pullulan, methyl cellulose, ethyl cellulose, hydroxypropyl cellulose, hydroxylpropylmethyl cellulose, cellulose acetate phthalate), sweeteners (e.g., aspartame, acesulfame potassium, sucralose, sorbitol, xylitol, Magnasweet, thaumatin), flavoring agents of artificial or natural origin, coloring agents, and combinations thereof. One or more pH modifier or buffering agent may additionally be added, which may include, but not be limited to, an inorganic acid (e.g., hydrochloric acid, sulfuric acid, phosphoric acid), an inorganic base (e.g., sodium hydroxide, potassium hydroxide, calcium hydroxide), an organic acid (e.g., citric acid, acetic acid, tartaric acid, succinic acid, boric acid, edetic acid, glucuronic acid, glutaric acid, malic acid, formic acid, gluconic acid, ascorbic acid or fatty acids), and/or an organic base (e.g., ethanolamine, triethanolamine), all of which may be used either with or without a corresponding counterion (i.e., salt of inorganic acid, salt of organic acid or salt of organic base). One of ordinary skill in the art can readily determine an appropriate amount of other pharmaceutical excipients if present in the solution/nanosuspension of step (a).

Fish gelatin suitable for use in the present invention is any non-hydrolyzed gelatin extracted from fish that is non-gelling when prepared as a dilute solution—in other words, any fish gelatin generally regarded by one of ordinary skill in the art as non-gelling and non-hydrolyzed. In the context of gelatin description, dilute preferably refers to a gelatin concentration of approximately 10% or less in water. Fish gelatin used in the present invention may comprise a single grade or mixtures of multiple fish gelatin grades, all of which are non-gelling and non-hydrolyzed. "Multiple" as used herein refers to more than one, i.e., two, three, four, five, etc. Fish gelatin can be obtained from commercial suppliers such as Norland Products Inc. (Cranbury, N.J.) who distribute two grades of fish gelatin: dry fish gelatin (DFG) and standard molecular weight (SMW) fish gelatin. The amount of fish gelatin present in the solution of step (a) preferably ranges from about 0.1% to about 30%, more preferably from about 0.5% to about 20%, and most preferably from about 1.0% to about 10% by weight of the solution.

Any pharmaceutically active ingredient that exists in the solid state at room temperature may be used for purposes of the present invention. As used herein, "pharmaceutically active ingredient" refers to a chemical entity possessing pharmacological activity that shows potential or has proven application for use as a pharmaceutical product or to a drug product that may be used in the diagnosis, cure, mitigation, treatment or prevention of disease. Most advantageously, the present invention would be used to formulate pharmaceutically active ingredients with poor water solubility. The term "poor solubility" is readily understood by one of ordinary skill in the art and is defined in many ways. One common definition of "poor solubility" is a solid-state pharmaceutically active ingredient whose solubility is less than about 1 mg/mL in aqueous phase. The criteria of <1 mg/mL is identified based on intrinsic solubility data, i.e., data generated on a pure, stable form of the pharmaceutically active ingredient whose solubility is determined at ambient temperature either in pure water or water containing only buffering agents to control pH at a value between approximately 1 to 8. Suitable pharmaceutically active ingredients include, without limitation, nonsteroidal anti-inflammatory drugs (NSAIDs, e.g., aspirin, ibuprofen, naproxen, indomethacin, diclofenac, nabumetone), analgesics (e.g., acetaminophen, phenacetin), 5-alpha-reductase inhibitors, 5-aminosalicylates, 5HT3 receptor antagonists, steroids, bronchodilators, aldosterone receptor antagonists, alkylating agents, alpha-glucosidase inhibitors, amebicides, aminoglycosides, androgens and anabolic steroids, angiotensin converting enzyme (ACE) inhibitors, angiotensin II inhibitors, anorexiants, antacids, anthelmintics, anti-infectives, anti-adrenergic agents, anti-anginal agents, anti-arrhythmics, antibiotics, anti-cholinergics, anti-coagulants, anti-convulsants, anti-depressants, anti-diabetic agents, anti-diarrheals, anti-fungals, anti-gout agents, anti-histamines, anti-hyperlipidemic agents, anti-hyperuricemic agents, anti-malarial agents, anti-metabolites, anti-migraine agents, anti-parkinson agents, anti-platelet agents, anti-bacterials, anti-psoriatics, anti-psychotics, anti-rheumatics, antiseptic and germicides, anti-viral agents, anxiolytics, sedatives, and hypnotics, anti-convulsants, beta-adrenergic blocking agents, bile acid sequestrants, bisphosphonates, bronchodilators, calcium channel blocking agents, carbonic anhydrase inhibitors, cephalosporins, chelating agents, chemokine recept agonists, chemokine receptor antagonists, chloride channel activators, cholesterol absorption inhibitors, cholesterol lowering agents (e.g., fenofibrate, fenofibric acid), cholinergic agonists, cholinesterase inhibitors, contraceptives, cox-2 inhibitors, decongestants, dipeptidyl peptidase 4 inhibitors, diuretics, dopaminergic agents, factor Xa inhibitors, gamma-aminobutyric acid analogs, gamma-aminobutyric acid reuptake inhibitors, gastrointestinal agents, anesthetics and other pain-modulating agents, glycoprotein platelet inhibitors, *H. pylori* eradication agents, histamine receptor antagonists, hormones, immunologic agents, immunosuppressive agents, impotence agents, incretin mimetics, inotropic agents, ketolides, laxatives, leukotriene modifiers, meglitinides, metabolic agents, methylxanthines, mineralocorticoids, monoamine oxidase inhibitors, mTOR kinase inhibitors, muscle relaxants, neuraminidase inhibitors, neuromuscular blocking agents, norepinephrine reuptake inhibitors, norepinephrine-dopamine reuptake inhibitors, nucleoside reverse transcriptase inhibitors (NRTIs), non-nucleoside reverse transcriptase inhibitors (NNRTIs), penicillins, peripheral opioid receptor antagonists, peripheral vasodilators, peripherally acting anti-obesity agents, prolactin inhibitors, protease inhibitors, proton pump inhibitors, psychotherapeutic agents, renin inhibitors, selective serotonin reuptake inhibitors, serotonin-norepinephrine reuptake inhibitors, serotoninergic neuroenteric modulators, statins, thrombin inhibitors, thrombolytics, thyroid drugs, tumor necrosis factor (TNF) inhibitors, tyrosine kinase inhibitors, vasodilators, vasopressin antagonists, vitamins, anti-epileptics, anti-hypertensive agents, anti-muscarinic agents, anti-neoplastic agents, anti-protozoal agents, anti-rheumatics, anti-thyroid agents, neuroleptics, cardiac inotropic agents, cough suppressants, cytotoxics, enzymes, lipid regulating agents, nitrates, nutritional agents, oral vaccines, proteins, peptides, recombinant drugs, stimulants and combinations thereof. A description of the marketed pharmaceutical active ingredients that fall into these classes of drugs can be found in Martindale; The Complete Drug Reference (The Pharmaceutical Press 35th ed. 2007), the disclosure of which is hereby incorporated by reference in its entirety. Also a list of specific examples of many of these classes may be found in U.S. Pat. No. 6,709,669, the disclosure of which is hereby incorporated by reference in its entirety.

The amount of pharmaceutically active ingredient present in the solution of step (a) preferably ranges from about 1% to about 50%, more preferably from about 2% to about 45%, and most preferably from about 5% to about 40% by weight of the solution. The amount of pharmaceutically active ingredient in the solution/nanosuspension of step (a) is an amount appropriate to provide a pharmaceutically effective amount of the pharmaceutically active ingredient in the oral solid dosage form of the finished product. As used herein, "pharmaceutically effective amount" refers to an amount required to bring about a desired pharmacological effect in diagnosis, cure, mitigation, treatment or prevention. One of ordinary skill in the art can readily determine an appropriate pharmaceutically effective amount.

During step (a) of the method of the invention, the suspension may be recycled if necessary and the process of particle size reduction continued until the desired nanoparticle size of the active ingredient is obtained. The size of the nanoparticles within the nanosuspension is typically measured using well known techniques, such as laser light diffraction methodology using, e.g., a Malvern Mastersizer 2000 particle size analyzer (Malvern Instruments, Westborough Mass.). Particle size measurements are typically described using parameters such as d50, a parameter that represents the size above and below which one finds 50% of the volume of all particles, also known as the volume weighted median. Accordingly, d50 represents a median particle size value. According to the invention, the solution is milled until a d50 ranging preferably from about 1 nm to about 900 nm, more preferably from about 10 nm to about 800 nm, and most preferably from about 50 nm to about 700 nm is achieved.

Once a nanosuspension is obtained, certain optional steps may be performed prior to step (b) of the present inventive method. For example, the nanosuspension may be diluted to a desired volume for purposes such as achieving a particular dosage amount in a finished product. As another example, at least one additional pharmaceutical excipient may be added. Such an additional pharmaceutical excipient added after achieving the nanosuspension may provide functionality unrelated to nanoparticle stabilization, since one of the benefits of the present invention is the ability to go from step (a) to step (b) without the need to add any additional nanoparticle stabilizer such as a polymeric or ionic stabilizer. Accordingly, in certain embodiments of the present invention, no additional nanoparticle stabilizers are added to the nanosuspension of step (a) or during step (b). At the same time, however, one of ordinary skill in the art will readily understand that many pharmaceutical excipients are dual- or multi-functional. Accordingly, pharmaceutical excipients, which may have recognized nanoparticle stabilization properties, may be added to provide other functionality. Examples of such pharmaceutical excipients include, but are not limited to, bulking agents (e.g., lactose monohydrate, anhydrous lactose, sucrose, trehalose, fructose, glucose, maltose, mannitol, isomalt, glycine, maltodextrin, microcrystalline cellulose), chemical stability enhancers (e.g., antioxidants, chelating agents, ion-exchange resins, α-, β-, or γ-cyclodextrins or substituted ring α-, β-, or γ-cyclodextrins) disintegrants (e.g., croscarmellose sodium, crospovidone, sodium starch glycolate, starch, modified starch), viscosity modifiers (e.g., bovine gelatin, porcine gelatin, alginates, carrageenan gum, gellan gum, guar gum, xanthan gum), sweeteners (e.g., aspartame, acesulfame potassium, sucralose, sorbitol, xylitol, Magnasweet, thaumatin), flavoring agents of artificial or natural origin, coloring agents, pH modifiers, and combinations thereof. One of ordinary skill in the art can readily determine an appropriate amount of other pharmaceutical excipients if added to the nanosuspension of step (a) prior to or during step (b).

In the second step of the present inventive method, the nanosuspension of step (a) is freeze-dried to form the oral solid dosage form. In a preferred embodiment of the invention, the nanosuspension of step (a) is dispensed into single unit doses prior to freeze-drying. Dispensing can be performed using any manual or automatic process that accurately delivers known volume or mass of suspension, such as a positive displacement pipette or a peristaltic dosing pump set. The nanosuspension of step (a) can be dosed into any receptacle that can be transferred to a freeze-drier and withstand the freeze-drying process, such as, e.g., bulk trays with or without pockets, unit-dose vials or a pre-formed dosage device (e.g., syringe). The most common example is a pre-formed tray of blister pockets or molds that will confer defined dimensions and shape onto the freeze-dried finished product. Freeze-drying, according to the present invention, is accomplished in any conventional manner using well known techniques. Freeze-drying is defined as any process that sequentially freezes the solvent phase (typically water) within product to form solid phase (freezing), followed by drying of the frozen phase under vacuum to cause removal of solvent (typically water) via sublimation (lyophilization). The term lyophilization can also be used to describe the freeze-drying process. The duration of freezing and drying steps, and the additional requirement of holding or annealing times either prior to or following either process step will be dictated by the specific properties of a given product and readily determined by one of ordinary skill in the art. As is recognized in the field, the freezing and drying steps can be performed using separate equipment or the same equipment as needed. For example, dispensed nanosuspension may be frozen using a static freezer unit (e.g., Cryo Freezer CM2000 made by Air Products and Chemicals Inc., Allentown, Pa.) or using a freeze-tunnel such as is made by Air Products and Chemicals, Inc. Frozen nanosuspension can be transferred to a pre-cooled lyophilizer, provided that necessary handling precautions are taken to maintain the product in the frozen state when transferring product between the freezer and a pre-cooled lyophilizer. Examples of lyophilizers suited for the present invention are the FTS Lyostar II (SP Industries, Warminster, Pa.) or Usifroid SMH90 (Usifroid, Paris, France), although any lyophilizer that has the capability to control shelf-temperature and chamber pressure with time such as to cause ice sublimation will be suitable for this purpose. It is also possible to perform both freezing and drying steps using only a lyophilizer such as the FTS Lyostar II or Usifroid SMH90, so long as the equipment has functionality to freeze product at the required rate and to the required temperature. For the present invention, either option of using separate freezer and lyophilizer or a lyophilizer alone are feasible.

It is well-recognized in the field that the rate of ice formation during freezing impacts the physical properties of freeze-dried materials. Generally, slower rates of cooling produce large ice crystals that, following drying, result in larger open channels or pores in the freeze-dried solid structure. Although large channels may seem desirable, such a structure often lacks physical robustness so faster cooling rates can be desirable. Therefore, freezing conditions must be carefully selected to form a viable freeze-dried product. In case of freeze-dried nanosuspensions, the greatest risk of nanoparticle aggregation is known to exist on freezing, as the freezing phenomenon generates significant mechanical stress and thermal energy in a local environment, i.e., in and around the surfaces of the suspended nanoparticles. Recognizing the sensitivity of nanoparticles to freezing, as well as the criticality of freezing in determining finished product attributes, it is notable that a single excipient, fish gelatin, can function so effectively as a nanoparticle stabilizer and produce freeze-dried matrices with favorable wetting and disintegration properties.

Without wishing to be bound by theory, it is believed that fish gelatin acts as a stabilizer both during the milling step and during the freeze-drying step. The effectiveness of fish gelatin as a performance aid during both these steps was completely unexpected. As will be seen from the examples and comparative examples below, the use of other types of gelatin, for example, bovine gelatin, in the present process, did not yield a stabilized oral solid dosage form. As used herein, "stabilized" refers to a dosage form containing nanoparticles that maintain pharmaceutically equivalent particle size during processing and upon extended storage. The definition of pharmaceutically equivalent particle size for nanoparticles may differ according to the properties and use of a product, but general guidance is that the d50 particle size remains within a ±150 nm range of a reference particle size and less than 1 micron. One of ordinary skill in the art will readily understand the term "pharmaceutically equivalent", i.e., equivalent in terms of pharmaceutical effectiveness.

Advantageously, the use of fish gelatin also avoids the problem of unpleasant taste associated with other commonly used ionic stabilizers such as, polysorbate 80 and sodium lauryl sulfate (SLS). In a preferred embodiment of this invention, the solid oral dosage form containing nanoparticles is substantially free of conventional ionic stabilizers such as polysorbate 80 and sodium lauryl sulfate. As used herein, "substantially free" refers to less than about 0.1% by weight of any such stabilizer in the solid oral dosage form of the invention. The present process also provides commercial efficiency and a simplified manufacturing procedure as no significant modifications of the nanosuspension are required mid-process, such as, prior to the freeze-drying step. In other words, no further excipients are required specifically for step (b), the freeze-drying step.

The inventors have found that the opportunity to dispense nanosuspension into pre-formed blisters, followed by freeze-drying of suspension in pre-formed blisters, provides an efficient means of preparing freeze-dried tablets containing nanoparticles directly into a pharmaceutically acceptable packaging material. Most advantageous is the opportunity to use a moisture-protective packaging material to make pre-formed blisters, as freeze-dried products are well-known to be moisture sensitive on storage. Alternatively, freeze-dried tablets containing nanoparticles can be removed from the tray pockets used during step (b) of this process and further processed and packaged to generate a viable finished product.

In a second embodiment of the invention, an oral solid dosage form containing nanoparticles is made by the process of the first embodiment of the invention described above. And a third embodiment of the invention is directed to a freeze-dried, oral solid dosage form comprising at least one nanoparticulate pharmaceutically active ingredient and fish gelatin. Details with regard to the identification of the fish gelatin, pharmaceutically active ingredient, and optional additional excipients are the same as described above with respect to the first embodiment.

The d50 for the nanoparticulate pharmaceutically active ingredient of the solid oral dosage form of the present invention ranges preferably from about 1 nm to about 900 nm, more preferably from about 10 nm to about 800 nm, and most preferably from about 50 nm to about 700 nm. The amount of fish gelatin present in the solid oral dosage form of the second or third embodiment of the invention preferably ranges from about 0.5% to about 99%, more preferably from about 1% to about 75%, and most preferably from about 5% to about 50% by weight of the solid oral dosage form. The amount of pharmaceutically active ingredient present in the solid oral dosage form of the second or third embodiment of the invention is a pharmaceutically effective amount as defined above and preferably ranges from about 0.1% to about 90%, more preferably from about 1% to about 80%, and most preferably from about 2% to about 75% by weight of the solid oral dosage form.

The solid oral dosage forms of the present invention may exhibit fast disintegration. As used herein, "fast disintegration" refers to a disintegration time measured using in vitro test conditions (e.g., USP disintegration apparatus with an aqueous media at 37° C.) of preferably 3 minutes or less, and more preferably 2 minutes or less, and most preferably 1 minute or less. The explanation for this physical property is that the highly porous solid structure generated by freeze-drying and more specifically lyophilization enhances disintegration properties of the solid. This attribute of the finished product is particularly beneficial for dosage forms containing nanoparticles, because disintegration is a prerequisite to nanoparticle dissolution and absorption of pharmaceutically active ingredient in vivo. Recognizing that the primary objective of developing a nanoparticulate dosage form is to increase the rate and extent of pharmaceutically active ingredient dissolution, the fast wetting and fast disintegration behavior will further enable a high performing product to be produced. It will be clear to those skilled in the art that poorly soluble pharmaceutically active ingredients are most prone to poor wetting and disintegration behavior, so achieving rapid disintegration with poorly soluble materials is a notable benefit of the freeze-dried dosage form of the present invention. Importantly, the rapid disintegration of these nanoparticulate dosage forms and nanoparticle size are both maintained following extended storage for 3 months or more at 25° C. The nanoparticle equivalency in solid dosage forms aged for 3 months or more further shows that fish gelatin enables formation of a physically robust dosage form.

The disintegration time targeted for a product made using the present invention can be manipulated to achieve specific disintegration properties that suit pharmacokinetic needs as well as patient requirements. Such manipulation will be achieved by varying formulation and process parameters such as drug loading, excipient content, type of excipients in addition to fish gelatin, and also unit size and dimensions. The freeze-dried end product containing nanoparticles may fulfill multiple product categories defined in the industry including, but not limited to, orally disintegrating tablets, orodispersible tablets, immediate-release tablets, controlled-release tablets, chewable tablets, sub-lingual tablets, buccal tablets, bioadhesive tablets, caplets, lozenges, powder for reconstitution, granule for reconstitution, or a tablet for reconstitution. The various product categories are dictated by government regulatory agencies as well as patient expectations, but all possible products generated using this invention would comprise a freeze-dried oral solid dosage form comprising at least one nanoparticulate pharmaceutically active ingredient and fish gelatin.

Specific embodiments of the invention will now be demonstrated by reference to the following examples. It should be understood that these examples are disclosed by way of illustrating the invention and should not be taken in any way to limit the scope of the present invention.

EXAMPLES 1A and 1B

An oral solid dosage form comprising the active ingredient naproxen and excipients fish gelatin as nanostabilizer (SMW fish gelatin grade from Norland Products Inc.—Example 1A; and DFG grade from Norland Products Inc.—Example 1B) and mannitol as bulking agent was prepared. An aqueous solution of 5% fish gelatin and 3% mannitol was prepared; then naproxen was added to this solution to form a suspension slurry. The suspension slurry was charged into a 600 cc chamber-size Dyno® Mill containing zirconium milling media. Naproxen concentration in the milling slurry was 15% by weight. Milling was performed on recirculating suspension for 1.5 hours using the default milling conditions for this equipment. The resultant bulk nanosuspension was discharged from the mill, and 250 mg unit doses were accurately dispensed into 0.25 mL capacity blister pockets using an IVEK pump controlled using a Digispense unit. Blister pockets were frozen in an Air Products CM2000 freezer using liquid nitrogen as coolant and a 3 minute freezing time, then held in a freezer until transfer to pre-cooled freeze-drier shelves. In a Lyostar II freeze-drier, drying was performed using a vacuum of less than 500 mTorr. The prepared oral solid dosage forms contained naproxen particles with particle size parameters set forth in Table 1 below. Particle size data were generated for this example and all examples using a Malvern Mastersizer 2000 calibrated on the same day using NIST standards in the submicron range. Aqueous dispersant was used in a sonication mode for analysis of all nanosuspension and solid oral dosage form testing.

TABLE 1

| Sample Information | d50 |
|---|---|
| unmilled naproxen | 22 μm |
| Example 1A | |
| after milling for 1.5 hr | 164 nm |
| freeze-dried tablet manufactured using fish gelatin | 167 nm |
| Example 1B | |
| after milling for 1.5 hr | 205 nm |
| freeze-dried tablet manufactured using fish gelatin | 209 nm |

As seen in the Table 1, two different grades of fish gelatin were effective nanoparticle stabilizers both during nanomilling and in freeze-dried units of an acidic poorly soluble drug such as naproxen.

EXAMPLE 2

An oral solid dosage form comprising the active ingredient indomethacin and excipients fish gelatin as nanostabilizer (DFG grade from Norland Products Inc.) and mannitol as bulking agent was prepared. An aqueous solution of 5% fish gelatin and 3% mannitol was prepared; then indomethacin was added to this solution to form a suspension slurry. The suspension slurry was charged into a 600 cc chamber-size Dyno® Mill containing zirconium milling media. Indomethacin concentration in the milling slurry was 15% by weight. Milling was performed on recirculating suspension for 1.5 hours using the default milling conditions for this equipment. The resultant bulk nanosuspension was discharged from the mill, and 250 mg unit doses were accurately dispensed into 0.25 mL capacity blister pockets using an IVEK pump controlled using a Digispense unit. Blister pockets were frozen in an Air Products CM2000 freezer using liquid nitrogen as coolant and a 3 minute freezing time, then held in a freezer until transfer to pre-cooled freeze-drier shelves. In a Lyostar II freeze-drier, drying was performed using a vacuum of less than 500 mTorr. The prepared oral solid dosage forms contained indomethacin particles with particle size parameters set forth in Table 2 below.

TABLE 2

| Sample Information | d50 |
| --- | --- |
| unmilled indomethacin | 37 μm |
| after milling for 1.5 hr | 151 nm |
| freeze-dried tablet manufactured using fish gelatin | 142 nm |

As seen in the Table 2, fish gelatin was an effective nanoparticle stabilizer during nanomilling and in freeze-dried units of an acidic poorly soluble drug such as indomethacin.

EXAMPLE 3

An oral solid dosage form comprising the active ingredient phenacetin and excipients fish gelatin (SMW fish gelatin grade from Norland Products Inc.) and mannitol was prepared. An aqueous solution of 5% fish gelatin and 3% mannitol was prepared; then phenacetin was added to this solution to form a suspension slurry. The suspension slurry was charged into a 600 cc chamber-size Dyno® Mill containing zirconium milling media. Phenacetin concentration in the milling slurry was 15% by weight. Milling was performed on recirculating suspension for 1.5 hours using the default milling conditions for this equipment. The resultant bulk nanosuspension was discharged from the mill, and 250 mg unit doses were accurately dispensed into 0.25 mL capacity blister pockets using an IVEK pump controlled using a Digispense unit. Blister pockets were frozen in an Air Products CM2000 freezer using liquid nitrogen as coolant and a 3 minute freezing time, then held in a freezer until transfer to pre-cooled freeze-drier shelves. In a Lyostar II freeze-drier, drying was performed using a vacuum of less than 500 mTorr. The prepared oral solid dosage forms contained phenacetin particles with particle size parameters set forth in Table 3 below.

TABLE 3

| Sample Information | d50 |
| --- | --- |
| unmilled phenacetin | 83 μm |
| after milling for 1.5 hr | 315 nm |
| freeze-dried tablet manufactured using fish gelatin | 324 nm |

As seen in Table 3, fish gelatin was an effective nanoparticle stabilizer during milling and also upon freeze-drying even for a basic drug such as phenacetin. These data suggest fish gelatin stabilization is viable for pharmaceutically active ingredients possessing different acid/base properties.

EXAMPLE 4

An oral solid dosage form comprising the active ingredient fenofibrate and fish gelatin as nanostabilizer (DFG grade from Norland Products Inc.) was prepared with additional pharmaceutical excipients. An aqueous solution of 5% fish gelatin, 3% mannitol, 0.5% sucralose and 0.5% mint flavor was prepared; then fenofibrate was added to this solution to form a suspension slurry. The suspension slurry was charged into a 600 cc chamber-size Dyno® Mill containing zirconium milling media. Fenofibrate concentration in the milling slurry was 14.5% by weight. Milling was performed on recirculating suspension for 2.5 hours using the default milling conditions for this equipment. The resultant bulk nanosuspension was discharged from the mill, and 250 mg unit doses were accurately dispensed into 0.25 mL capacity blister pockets using an IVEK pump controlled using a Digispense unit. Blister pockets were frozen in an Air Products CM2000 freezer using liquid nitrogen as coolant and a 3 minute freezing time, then held in a freezer until transfer to pre-cooled freeze-drier shelves. In a Lyostar II freeze-drier, drying was performed using a vacuum of less than 500 mTorr. The prepared oral solid dosage forms contained fenofibrate particles with particle size parameters set forth in Table 4 below.

TABLE 4

| Sample Information | d50 |
| --- | --- |
| unmilled fenofibrate | 30 μm |
| After milling for 2 hrs | 162 nm |
| freeze-dried tablet manufactured using fish gelatin | 167 nm |

As seen in Table 4, fish gelatin was an effective nanoparticle stabilizer through milling and freeze-drying for fenofibrate, a pharmaceutically active ingredient that is poorly water soluble as the free acid.

EXAMPLE 5

An oral solid dosage form comprising the active ingredient naproxen and the excipient fish gelatin (DFG grade from Norland Products Inc.) was prepared. An aqueous solution of 5% fish gelatin was prepared; then naproxen was added to this solution to form a suspension slurry. The suspension slurry was charged into a 600 cc chamber-size Dyno® Mill containing zirconium milling media. Naproxen concentration in the milling slurry was 15% by weight. Milling was performed on recirculating suspension for 1.5 hours using the default milling conditions for this equipment. The resultant bulk nanosuspension was discharged from the mill, and 250 mg unit doses were accurately dispensed into 0.25 mL capacity blister pockets using an IVEK pump controlled using a Digispense unit. Blister pockets were frozen in an Air Products CM2000 freezer using liquid nitrogen as coolant and a 3 minute freezing time, then held in a freezer until transfer to pre-cooled freeze-drier shelves. In a Lyostar II freeze-drier, drying was performed using a vacuum of less than 500 mTorr. The prepared oral solid dosage forms contained naproxen particles with particle size parameters set forth in Table 5 below.

TABLE 5

| Sample Information | d50 |
| --- | --- |
| unmilled naproxen | 22 μm |
| after milling for 1.5 hr | 167 nm |
| freeze-dried tablet manufactured using fish gelatin | 177 nm |

As seen in Table 5, fish gelatin by itself is sufficient to stabilize nanoparticles during nanomilling and also in a freeze-dried solid oral dosage form. Mannitol is not needed to achieve stabilization of nanoparticles in this product.

EXAMPLE 6

An oral solid dosage form comprising the active ingredient naproxen and excipients fish gelatin as nanostabilizer (DFG grade from Norland Products Inc.) and mannitol as bulking agent was prepared. An aqueous solution of 3% fish gelatin and 2% mannitol was prepared; then naproxen was added to this solution to form a suspension slurry. The suspension slurry was charged into a 600 cc chamber-size Dyno® Mill containing zirconium milling media. Naproxen concentration in the milling slurry was 15% by weight. Milling was performed on recirculating suspension for 1.5 hours using the default milling conditions for this equipment. The resultant bulk nanosuspension was discharged from the mill, and 250 mg unit doses were accurately dispensed into 0.25 mL capacity blister pockets using an IVEK pump controlled using a Digispense unit. Blister pockets were frozen in an Air Products CM2000 freezer using liquid nitrogen as coolant and a 3 minute freezing time, then held in a freezer until transfer to pre-cooled freeze-drier shelves. In a Lyostar II freeze-drier, drying was performed using a vacuum of less than 500 mTorr. The prepared oral solid dosage forms contained naproxen particles with particle size parameters set forth in Table 6 below.

TABLE 6

| Sample Information | d50 |
| --- | --- |
| unmilled naproxen | 22 μm |
| after milling for 1.5 hrs with fish gelatin | 187 nm |
| Freeze-dried tablet manufactured using fish gelatin | 191 nm |

As seen in Table 6, modified concentration of fish gelatin (reduced relative to Examples 1A and 1B to 3%) was effective in stabilizing nanoparticles during nanomilling and in a freeze-dried solid oral dosage form.

COMPARATIVE EXAMPLES 1A and 1B

An oral solid dosage form comprising the active ingredient naproxen and excipient bovine gelatin (low bloom grade of acid hide gelatin provided by Gelita —1A; low bloom grade of acid hide gelatin sourced from Weishardt—1B) was prepared. An aqueous solution of 3% bovine gelatin and 2% mannitol was prepared; then naproxen was added to this solution to form a suspension slurry. The suspension slurry was charged into a 600 cc chamber-size Dyno® Mill containing zirconium milling media. Naproxen concentration in the milling slurry was 15% by weight. Milling was performed on recirculating suspension for 1.5 hours using the default milling conditions for this equipment. The resultant bulk nanosuspension was discharged from the mill, and 250 mg unit doses were accurately dispensed into 0.25 mL capacity blister pockets using an IVEK pump controlled using a Digispense unit. Blister pockets were frozen in an Air Products CM2000 freezer using liquid nitrogen as coolant and a 3 minute freezing time, then held in a freezer until transfer to pre-cooled freeze-drier shelves. In a Lyostar II freeze-drier, drying was performed using a vacuum of less than 500 mTorr. The prepared oral solid dosage forms contained naproxen particles with particle size parameters set forth in Table 7 below.

TABLE 7

| Sample Information | d50 |
| --- | --- |
| unmilled naproxen | 22 μm |
| Comparative Example 1A | |
| after milling for 1.5 hr | 177 nm |
| freeze-dried tablet manufactured using bovine gelatin | 21 μm |
| Comparative Example 1B | |
| after milling for 1.5 hr | 193 nm |
| freeze-dried tablet manufactured using bovine gelatin | 13 μm |

As seen in Table 7, bovine gelatin enabled nanoparticle formation on nanomilling. However, neither of the two bovine gelatins stabilized nanoparticles in freeze-dried solid oral dosage form.

COMPARATIVE EXAMPLE 2

An oral solid dosage form comprising the active ingredient indomethacin and excipient bovine gelatin (low bloom grade of acid hide gelatin provided by Gelita) was prepared. An aqueous solution of 3% bovine gelatin and 2% mannitol was prepared; then indomethacin was added to this solution to form a suspension slurry. The suspension slurry was charged into a 600 cc chamber-size Dyno® Mill containing zirconium milling media. Indomethacin concentration in the milling slurry was 15% by weight. Milling was performed on recirculating suspension for 1.5 hours using the default milling conditions for this equipment. The resultant bulk nanosuspension was discharged from the mill, and 250 mg unit doses were accurately dispensed into 0.25 mL capacity blister pockets using an IVEK pump controlled using a Digispense unit. Blister pockets were frozen in an Air Products CM2000 freezer using liquid nitrogen as coolant and a 3 minute freezing time, then held in a freezer until transfer to pre-cooled freeze-drier shelves. In a Lyostar II freeze-drier, drying was performed using a vacuum of less than 500 mTorr. The prepared oral solid dosage forms contained indomethacin particles with particle size parameters set forth in Table 8 below.

TABLE 8

| Sample Information | d50 |
| --- | --- |
| unmilled indomethacin | 37 μm |
| after milling for 1.5 hrs | 159 nm |
| freeze-dried tablet manufactured using bovine gelatin | 30 μm |

As seen in Table 8, bovine gelatin enabled indomethacin nanoparticle formation on nanomilling. However, nanoparticles were not retained in the freeze-dried solid oral dosage form with d50 increasing to above one micron.

Testing

A comparison of the disintegration times of the oral solid dosage forms of the present examples under the specified conditions are set forth in Table 9 below.

TABLE 9

| Example Number (and drug) | Disintegration Time After Manufacture | Disintegration Time on Aging | d50 After Manufacture | d50 After Aging |
| --- | --- | --- | --- | --- |
| Example 1A (Naproxen) | 9 seconds | 11 seconds* | 167 nm | 166 nm* |
| Example 1B (Naproxen) | 2 seconds | 3 seconds** | 209 nm | 196 nm** |
| Example 2 (Indomethacin) | 8 seconds | 10 seconds** | 142 nm | 161 nm** |
| Example 3 (Phenacetin) | 2 seconds | not measured | 324 nm | not measured |
| Example 4 (Fenofibrate) | 4 seconds | not measured | 167 nm | not measured |
| Example 5 (Naproxen) | 6 seconds | 7 seconds* | 177 nm | 173 nm* |
| Example 6 (Naproxen) | 5 seconds | not measured | 191 nm | not measured |

*aged for 3 months
**aged for 6 months

As seen in Table 9, disintegration times of 11 seconds or less were measured for the freeze-dried oral solid dosage forms, including selected prototypes that were subjected to aging for 3 months or more under controlled conditions. Disintegration time data were generated using USP in vitro disintegration test apparatus with 900 mL water at 37° C. used as disintegration test media. Five units were tested for each data set, and the reported disintegration time represents the time at which all 5 units disintegrated such that no palpable mass or solid remains. Those prototypes subjected to the aging experiment were also retested for particle size, and d50 data are also shown in Table 9. The repeat particle size data confirms that the nanoparticle size is maintained upon extended storage, where measured.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A method of preparing an oral solid dosage form of at least one pharmaceutically active ingredient consisting of nanoparticles, the process comprising the steps of:
   (a) adding the at least one pharmaceutically active ingredient to a solution containing a nanoparticle stabilizer to form a dispersion, wherein the nanoparticle stabilizer is a fish gelatin;
   (b) reducing the particle size of the dispersion to form a nanosuspension, wherein no additional nanoparticle stabilizer is added in step (b); and
   (c) freeze-drying the nanosuspension of step (b) to form the oral solid dosage form that maintains a pharmaceutically equivalent particle size to the nanosuspension of step (b), wherein no additional nanoparticle stabilizer is added in step (c), and wherein the d50 particle size of the oral solid dosage form is maintained upon extended storage.

2. The method of claim 1, wherein the fish gelatin is a nongelling, non-hydrolyzed fish gelatin or a combination of multiple non-gelling, nonhydrolyzed fish gelatins.

3. The method of claim 1, wherein the nanosuspension further comprises at least one pharmaceutical excipient.

4. The method of claim 3, wherein the at least one pharmaceutical excipient is selected from the group consisting of bulking agents, disintegrants, viscosity modifiers, sweeteners, flavoring agents, coloring agents, pH modifiers, and combinations thereof.

5. The method of claim 1, wherein the at least one pharmaceutically active ingredient has a measured solubility of less than 1 mg/mL.

6. A freeze-dried, oral solid dosage form of at least one pharmaceutically active ingredient consisting of nanoparticles made by a process comprising the steps of:
   (a) adding the at least one pharmaceutically active ingredient to a solution containing a nanoparticle stabilizer to form a dispersion, wherein the nanoparticle stabilizer is a fish gelatin;
   (b) reducing the particle size of the dispersion to form a nanosuspension; and
   (c) freeze-drying the nanosuspension of step (b), wherein the freeze-dried, oral solid dosage form maintains a pharmaceutically equivalent particle size of less than about 1 micron to the nanosuspension of step (b), wherein no additional nanoparticle stabilizer is added to the nanosuspension, and wherein the d50 particle size of the oral solid dosage form is maintained upon extended storage.

7. The oral solid dosage form of claim 6, wherein the fish gelatin is a non-gelling, non-hydrolyzed fish gelatin or a combination of multiple non-gelling, non-hydrolyzed fish gelatins.

8. The oral solid dosage form of claim 6, wherein the nanosuspension further comprises at least one pharmaceutical excipient.

9. The oral solid dosage form of claim 8, wherein the at least one pharmaceutical excipient is selected from the group consisting of bulking agents, disintegrants, viscosity modifiers, sweeteners, flavoring agents, coloring agents, pH modifiers, and combinations thereof.

10. The oral solid dosage form of claim 6, wherein the at least one pharmaceutically active ingredient has a measured solubility of less than 1 mg/mL.

11. A freeze-dried, oral solid dosage form consisting essentially of a nanoparticle stabilizer and at least one pharmaceutically active ingredient consisting of nanoparticles;
   wherein the nanoparticle stabilizer is fish gelatin,
   wherein no additional nanoparticle stabilizer is added to the nanosuspension,
   wherein the nanoparticles maintain a pharmaceutically equivalent particle size, and
   wherein the d50 particle size of the oral solid dosage form is maintained upon extended storage.

12. The freeze-dried, oral solid dosage form of claim 11, wherein the fish gelatin is a non-gelling, non-hydrolyzed fish gelatin or a combination of multiple non-gelling, non-hydrolyzed fish gelatins.

13. The freeze-dried, oral solid dosage form of claim 11, further comprising at least one pharmaceutical excipient.

14. The freeze-dried, oral solid dosage form of claim 13, wherein the at least one pharmaceutical excipient is selected from the group consisting of bulking agents, disintegrants, viscosity modifiers, sweeteners, flavoring agents, coloring agents, pH modifiers, and combinations thereof.

15. The freeze-dried, oral solid dosage form of claim 11, wherein the at least one pharmaceutically active ingredient has measured solubility of less than 1 mg/mL.

16. The oral solid dosage form of claim 6, wherein the pharmaceutically active ingredient is present in the dispersion of step (b) in a range of from about 1% to about 50% by weight of the dispersion.

17. The oral solid dosage form of claim 16, wherein the pharmaceutically active ingredient is present in the dispersion of step (b) in a range of from about 2% to about 45% by weight of the dispersion.

18. The oral solid dosage form of claim 17, wherein the pharmaceutically active ingredient is present in the dispersion of step (b) in a range of from about 5% to about 40% by weight of the dispersion.

19. A method of preparing an oral solid dosage form of at least one pharmaceutically active ingredient consisting of nanoparticles, the process comprising the steps of:
   (a) adding the at least one pharmaceutically active ingredient to a solution containing a nanoparticle stabilizer to form a dispersion, wherein the nanoparticle stabilizer is a fish gelatin;
   (b) reducing the particle size of the dispersion to form a nanosuspension, wherein the d50 particle size remains within a ±150 nm range of a reference particle and less than 1 micron, wherein no additional nanoparticle stabilizer is added in step (b); and (c) freeze-drying the nanosuspension of step (b) to form the oral solid dosage form that maintains a pharmaceutically equivalent particle size to the nanosuspension of step (b), wherein no additional nanoparticle stabilizer is added in step (c), and wherein the d50 particle size of the oral solid dosage form is maintained upon extended storage.

* * * * *